US007956164B2

(12) United States Patent
Har-Noy

(10) Patent No.: US 7,956,164 B2
(45) Date of Patent: *Jun. 7, 2011

(54) DEVICE FOR ENHANCING IMMUNOSTIMULATORY CAPABILITIES OF T-CELLS

(75) Inventor: Michael Har-Noy, Modi'in (IL)

(73) Assignee: Immunovative Therapies Ltd., Shoham (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/687,281

(22) Filed: Jan. 14, 2010

(65) Prior Publication Data
US 2010/0113753 A1 May 6, 2010

Related U.S. Application Data

(62) Division of application No. 11/066,133, filed on Feb. 24, 2005, now Pat. No. 7,678,572.

(60) Provisional application No. 60/547,966, filed on Feb. 26, 2004.

(51) Int. Cl.
C07K 16/00 (2006.01)

(52) U.S. Cl. ........... 530/387.1; 530/387.7; 530/391.1

(58) Field of Classification Search .......... None
See application file for complete search history.

(56) References Cited

U.S. PATENT DOCUMENTS

| 4,279,249 A | 7/1981 | Vert et al. |
| 5,126,132 A | 6/1992 | Rosenberg |
| 5,443,983 A | 8/1995 | Ochoa et al. |
| 5,766,920 A | 6/1998 | Babbitt et al. |
| 5,806,529 A | 9/1998 | Reisner et al. |
| 5,846,827 A | 12/1998 | Celis et al. |
| 6,040,177 A | 3/2000 | Riddell et al. |
| 6,194,207 B1 | 2/2001 | Bell et al. |
| 6,251,385 B1 | 6/2001 | Terman |
| 6,255,073 B1 | 7/2001 | Cai et al. |
| 6,352,694 B1 | 3/2002 | June et al. |
| 6,500,193 B1 | 12/2002 | Bezemer et al. |
| 6,511,511 B1 | 1/2003 | Slivka et al. |
| 6,514,286 B1 | 2/2003 | Leatherbury et al. |
| 6,534,055 B1 | 3/2003 | June et al. |
| 6,572,894 B2 | 6/2003 | Rossling et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,402,431 B2 | 7/2008 | Har-Noy |
| 7,435,592 B2 | 10/2008 | Har-Noy |
| 7,592,431 B2 * | 9/2009 | Har-Noy .......... 530/391.1 |
| 7,678,572 B2 | 3/2010 | Har-Noy |
| 2002/0127208 A1 | 9/2002 | Waller et al. |
| 2003/0004578 A1 | 1/2003 | Brown et al. |
| 2003/0175272 A1 | 9/2003 | Gruenberg |
| 2003/0215946 A1 | 11/2003 | Nair et al. |
| 2005/0065593 A1 | 3/2005 | Chu et al. |
| 2005/0191746 A1 | 9/2005 | Van et al. |
| 2006/0036331 A1 | 2/2006 | Lu et al. |
| 2006/0121021 A1 | 6/2006 | Hunig |
| 2007/0086996 A1 | 4/2007 | Har-Noy |

FOREIGN PATENT DOCUMENTS

| EP | 0319012 A2 | 6/1989 |
| WO | 9412196 A1 | 6/1994 |
| WO | 9746256 A1 | 12/1997 |
| WO | 9924045 A1 | 5/1999 |
| WO | 0162895 A2 | 8/2001 |
| WO | 03024989 | 3/2003 |
| WO | 03/038062 | 5/2003 |
| WO | 2004004768 A1 | 1/2004 |
| WO | 2005001074 A | 1/2005 |
| WO | 2005081982 A | 9/2005 |
| WO | 2005084276 A | 9/2005 |

OTHER PUBLICATIONS

Antin, J. H. et al. (1992). "Cytokine Dysregulation and Acute Graft-Versus-Host Disease." Blood, vol. 80, No. 12: pp. 2964-2968.
Anderson, P. et al. (1988). "Crosslinking CD3 with CD2 Using Sepharose-Immobilized Antibodies Enhances T Lymphocyte Proliferation." Cellular Immunology, vol. 115, No. 2: pp. 246-256.
Asselin-Paturel et al. (1998). "Quantitative Analysis of Th1, Th2 and TGF-β1 Cytokine Expression in Tumor, TIL and PBL of Non-Small Cell Lung Cancer Patients." Int. J. Cancer, vol. 77, No. 1: pp. 7-12.
Bachmann, M. F. et al. (1997). "Distinct Roles for LFA-1 and CD28 During Activation of Naive T Cells: Adhesion Versus Costimulation." Immunity, vol. 7, No. 4: pp. 549-557.
Banu, N. et al. (1999). "TGF-β1 down-regulates induced expression of both class II MHC and B7-1 on primary murine renal tubular epithelial cells." Kidney International, vol. 56, No. 3: pp. 985-994.
Baroja, M.L. et al. (1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogens." Cellular Immunology, vol. 120, No. 1: pp. 205-217.

(Continued)

Primary Examiner — Michail A Belyavskyi
(74) Attorney, Agent, or Firm — Z. Peter Sawicki; Westman, Champlin & Kelly, P.A.

(57) ABSTRACT

T-cells are generated with enhanced immunostimulatory capabilities for use in self therapy treatment protocols, by utilizing a biodegradable device with a biodegradable support that has one or more agents that are reactive to T-cell surface moieties. The biodegradable devices are mixed with the T-cells sufficiently so that the one or more agents cross-link with the T-cells' surface moieties and deliver a signal to the T-cells to enhance immunostimulatory capabilities.

13 Claims, No Drawings

OTHER PUBLICATIONS

Baxevanis, C. N. et al. (2000). "Compromised anti-tumor responses in tumor necrosis factor-α knockout mice." Eur. J. Immunol, vol. 30, No. 7: pp. 1957-1966.

Belardelli, F. et al. (2002). "Cytokines as a link between innate and adaptive antitumor immunity." Trends in Immunology, vol. 23 No. 4: pp. 201-208.

Blazar, B. R. et al. (1997). "Recent advances in graft-versus-host disease (GVHD) prevention." Immunological Reviews, vol. 157: pp. 79-109.

Blazar, B. R. et al. (1998). "Rapamycin Inhibits the Generation of Graft-Versus-Host Disease- and Graft-Versus-Leukemia-Causing T Cells by Interfering with the Production of Th1 or Th1 Cytotoxic Cytokines." Journal of Immunology, vol. 160, No. 11: pp. 5355-5365.

Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." Transplantation, vol. 63, No. 9: pp. 1307-1313.

Carpentier, A. F., G. Auf, et al (2003). "CpG-oligonucleotides for cancer immunotherapy : review of the literature and potential applications in malignant glioma." Front Biosci 8: E115-27.

Chambers, C. A. et al. (1999). "Costimulatory regulation of T cell function." Current Opinion in Cell Biology, vol. 11, No. 2: pp. 203-210.

Champlin, R., I. Khouri, et al. (1999). "Allogeneic hematopoietic transplantation as adoptive immunotherapy. Induction of graft-versus-malignancy as primary therapy." Hematol Oncol Clin North Am 13(5): 1041-57, vii-viii.

Champlin, R., K. van Besien, et al. (2000). "Allogeneic hematopoietic transplantation for chronic lymphocytic leukemia and lymphoma: potential for nonablative preparative regimens." Curr Oncol Rep 2(2): 182-91.

Chang, J. W., M. Peng, et al. (2000). "Induction of Th1 response by dendritic cells pulsed with autologous melanoma apoptotic bodies." Anticancer Res 20(3A): 1329-36.

Chen, Q. et al. (1994). "Production of IL-10 by Melanoma Cells: Examination of its Role in Immunosuppression Mediated by Melanoma." Int. J. Cancer, vol. 56, No. 5: pp. 755-760.

Childs, R. et al. (2002). "Nonmyeloablative Stem Cell Transplantation for Solid Tumors: Expanding the Application of Allogeneic Immunotherapy." Seminars in Hematology, vol. 39, No. 1: pp. 63-71.

Childs, R. et al. (2000). "Regression of metastatic renal-cell carcinoma after nonmyeloablative allogeneic peripheral-blood stem-cell transplantation." The New England Journal of Medicine, vol. 343, No. 11: pp. 750-758.

Childs, R. W. (2000). "Nonmyeloablative allogeneic peripheral blood stem-cell transplantation as immunotherapy for malignant diseases." Cancer J 6(3): 179-87.

Childs, R. W. (2002). "Immunotherapy of solid tumors: nonmyeloablative allogeneic stem cell transplantation." MedGenMed 4(3): 13.

Cierici, M. et al. (1993). "A TH1→TH2 switch is a critical step in the etiology of HIV infection." Immunology Today, vol. 14, No. 3: pp. 107-111.

Cohen, P. A., L. Peng, et al. (2000). "CD4+ T cells in adoptive immunotherapy and the indirect mechanism of tumor rejection." Crit Rev Immunol 20(1): 17-56.

Damle, N.K. et al. (1989). "Stimulation Via the CD3 and CD28 Molecules Induces Responsiveness to IL-4 in CD4+CD29+CD45R- Memory T Lymphocytes." The Journal of Immunology, vol. 143, No. 6: pp. 1761-1767.

Das, H., S. Imoto, et al. (2001). "Kinetic analysis of cytokine gene expression in patients with GVHD after donor lymphocyte infusion." Bone Marrow Transplant 27(4): 373-80.

Daubener, W. et al. (1995). "Establishment of T-helper type 1- and T-helper type 2-like human Toxoplasma antigen-specific T-cell clones." Immunology, vol. 86, No. 1: pp. 79-84.

Deeths, M. J. et al. (1999). "CD8+ T Cells Become Nonresponsive (Anergic) Following Activation in the Presence of Costimulation." The Journal of Immunology, vol. 163, No. 1: pp. 102-110.

De Vita, F., M. Orditura, et al. (2000). "Serum interleukin-10 is an independent prognostic factor in advanced solid tumors." Oncol Rep 7(2): 357-61.

de Waal Malefyt, R. et al. (1993). "Direct Effects of IL-10 on Subsets of Human CD4+ T Cell Clones and Resting T Cells. Specific Inhibition of IL-2 Production and Proliferation." The Journal of Immunology, vol. 150, No. 11: pp. 4754-4765.

D'Orazio, T. J. et al. (1998). "A Novel Role for TGF-β and IL-10 in the Induction of Immune Privilege." The Journal of Immunology, vol. 160, No. 5: 2089-2098.

Dudley, M. E. et al. (2002). "Cancer Regression and Autoimmunity in Patients After Clonal Repopulation with Antitumor Lymphocytes." Science, vol. 298, No. 5594: pp. 850-854.

Egeter, O. et al. (2000). "Eradication of Disseminated Lymphomas with CpG-DNA Activated T Helper Type 1 Cells from Nontransgenic Mice." Cancer Research, vol. 60, No. 6: 1515-1520.

Eibl, B. et al. (1996). "Evidence for a Graft-Versus-Tumor Effect in a Patient Treated With Marrow Ablative Chemotherapy and Allogeneic Bone Marrow Transplantation for Breast Cancer." Blood, vol. 88, No. 4: pp. 1501-1508.

Elsasser-Beile, U. et al. (1999). "Semiquantitative analysis of Th1 and Th2 cytokine expression in CD3+, CD4+, and CD8+ renal-cell-carcinoma-infiltrating lymphocytes." Cancer Immunol Immunother, vol. 48, No. 4: pp. 204-208.

Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." Biotherapy 9(4): 249-56.

Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." J Drug Targt 8(3): 173-84.

Fan, X. G., W. E. Liu, et al. (1998). "Circulating Th1 and Th2 cytokines in patients with hepatitis C virus infection." Mediators Inflamm 7(4): 295-7.

Finke, J. H., P. Rayman, et al. (1992). "Characterization of a human renal cell carcinoma specific cytotoxic CD8+ T cell line." J Immunother 11(1): 1-11.

Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." J Immunother Emphasis Tumor Immunol 15(2): 91-104.

Flanagan, D. L. et al. (1999). "Th1 Cytokines and NK Cells Participate in the Development of Murine Syngeneic Graft-Versus-Host Disease." The Journal of Immunology, vol. 163, No. 3: pp. 1170-1177.

Fowler, D. H., J. Breglio, et al. (1996). "Allospecific CD4+, Th1/Th2 and CD8+, Tc1/Tc2 populations in murine GVL: type I cells generate GVL and type II cells abrogate GVL." Biol Blood Marrow Transplant 2(3): 118-25.

Fowler, D. H. and R. E. Gress (2000). "Th2 and Tc2 cells in the regulation of GVHD, GVL, and graft rejection: considerations for the allogeneic transplantation therapy of leukemia and lymphoma." Leuk Lymphoma 38(3-4): 221-34.

Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." Bone Marrow Transplant 17(1): 13-8.

Freeman, G. J. et al. (2002). "Protect the killer: CTLs need defenses against the tumor." Nature Medicine, vol. 8, No. 8: pp. 787-789.

Friess, H., H. G. Beger, et al. (1996). "Treatment of advanced pancreatic cancer with mistletoe: results of a pilot trial." Anticancer Res 16(2): 915-20.

Fujimoto, T. et al. (1997). "Streptococcal Preparation OK-432 is a Potent Inducer of IL-12 and a T Helper Cell 1 Dominant State." The Journal of Immunology, vol. 158, No. 12: pp. 5619-5626.

Fujisao, S. et al. (1998). "Th1/Th2 balance alteration in the clinical course of a patient with pure red cell aplasia and thymoma." British Journal of Haematology, vol. 103, No. 2: pp. 308-310.

Gabrilovich, D. I. et al. (1996). "Dendritic Cells in Antitumor Immune Responses. II. Dendritic Cells Grown from Bone Marrow Precursors, but Not Mature DC from Tumor-Bearing Mice, Are Effective Antigen Carriers in the Therapy of Established Tumors." Cellular Immunology, vol. 170, No. 1: pp. 111-119.

Gale, R. P. et al. (1984). "How Does Bone-Marrow Transplantation Cure Leukaemia?" The Lancet, vol. 2, No. 8393: pp. 28-30.

Garlie, N.K., A.V. LeFever, et al. (1999). "T cells coactivated with immobilized anti-CD3 and anti-CD28 as potential immunotherapy for cancer." J Immunother 22(4): 336-45.

Geppert, T.D. et al. (1988). "Activation of T Lymphocytes by Immobilized Monoclonal Antibodies to CD3, Regulatory Influences of Monoclonal Antibodies to Additional T Cell Surface Determinants." J. Clin. Invest., vol. 81: pp. 1497-1505.

Ghosh, P., K. L. Komschlies, et al. (1995). "Gradual loss of T-helper 1 populations in spleen of mice during progressive tumor growth." J Natl Cancer Inst 87(19): 1478-83.

Gorelik, L., A. Prokhorova, et al. (1994). "Low-dose melphalan-induced shift in the production of a Th2-type cytokine to a Th1-type cytokine in mice bearing a large MOPC-315 tumor." Cancer Immunol Immunother 39(2): 117-26.

Grakoui, A. et al. (1999). "The Immunological Synapse: A Molecular Machine Controlling T Cell Activation." Science, vol. 285, No. 5425: pp. 221-227.

Granucci, F. et al. (2001). "Transcriptional reprogramming of dendritic cells by differentiation stimuli." Eur J Immunol, vol. 31, No. 9: pp. 2539-2546.

Grigg, A., P. Bardy, et al. (1999). "Fludarabine-based non-myeloablative chemotherapy followed by infusion of HLA-identical stem cells for relapsed leukaemia and lymphoma." Bone Marrow Transplant 23(2): 107-10.

Grohmann, U., M. C. Fioretti, et al. (1998). "Dendritic cells, interleukin 12, and CD4+ lymphocytes in the initiation of class I-restricted reactivity to a tumor/self peptide." Crit Rev Immunol 18(1-2): 87-98.

Hara, I., H. Hotta, et al. (1996). "Rejection of mouse renal cell carcinoma elicited by local secretion of interleukin-2." Jpn J Cancer Res 87(7): 724-9.

Heine, G. et al. (2002). "A shift in the Th(1)/Th(2) ratio accompanies the clinical remission of systemic lupus erythematosus in patients with end-stage renal disease." Nephrology Dialysis Transplantion, vol. 17, No. 10: pp. 1790-1794.

Heniford, B. T. et al. (1994). "Interleukin-8 Suppresses the Toxicity and Antitumor Effect of Interleukin-2," Journal of Surgical Research, vol. 56, No. 1: pp. 82-88.

Herlyn, D. and B. Birebent (1999). "Advances in cancer vaccine development." Ann Med 31(1): 66-78.

Horiguchi, S. et al. (1999). "Primary Chemically Induced Tumors Induce Profound Immunosuppression Concomitant with Apoptosis and Alterations in Signal Transduction in T Cells and NK Cells." Cancer Research, vol. 59, No. 12: pp. 2950-2956.

Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." Anticancer Res 18(5D): 3957-64.

Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." Cancer, vol. 85, No. 11: pp. 2359-2367.

Janes, P. W. et al. (1999). "Aggregation of Lipid Rafts Accompanies Signaling Via the T Cell Antigen Receptor." The Journal of Cell Biology, vol. 147, No. 2: pp. 447-461.

Jung, U. et al. (Nov. 2003). "CD3/CD28-costimulated T1 and 12 subsets: differential in vivo allosensitization generates distinct GVT and GVHD effects." Blood, vol. 1, No. 9: pp. 3439-3446.

Kadowaki, N. et al. (2002). "Natural Type I Interferon-Producing Cells as a Link Between Innate and Adaptive Immunity." Human Immunology, vol. 63, No. 12: pp. 1126-1132.

Kai, S. and H. Hare (2003). "Allogeneic hematopoietic stem cell transplantation." Therap Apher Dial 7(3): 285-91.

Kasakura, S. (1998). "[A role for T-helper type 1 and type 2 cytokines in the pathogenesis of various human diseases]," Rinsho Byori 46(9): 915-21.

Kitahara, S., M. Ikeda, et al. (1996). "Inhibition of head and neck metastatic and/or recurrent cancer by local administration of multi-cytokine inducer OK-432." J Laryngol Otol 110(5): 449-53.

Knoefel, B., K. Nuske, et al. (1997). "Renal cell carcinomas produce IL-6, IL-10, IL-11, and TGF-beta 1 in primary cultures and modulate T lymphocyte blast transformation." J Interferon Cytokine Res 17(2): 95-102.

Kobayashi, M. et al. (1998). "A Pathogenic Role of Th2 Cells and Their Cytokine Products on the Pulmonary Metastasis of Murine B16 Melanoma." The Journal of Immunology, vol. 160, No. 12: pp. 5869-5873.

Kobayashi, M., R. B. Pollard, et al. (1997). "Inhibition of pulmonary metastasis by Z-100, an immunomodulatory lipid-arabinomannan extracted from *Mycobacterium tuberculosis*, in mice inoculated with B16 melanoma." Anticancer Drugs 8(2): 156-63.

Lahn, M. et al. (1999). "Pro-Inflammatory and T Cell Inhibitory Cytokines Are Secreted at High Levels in Tumor Cell Cultures of Human Renal Cell Carcinoma." European Urology, vol. 35, No. 1: pp. 70-80.

Langenkamp, A. et al. (2000). "Kinetics of dendritic cell activation: impact on priming of TH1, TH2 and nonpolarized T cells." Nature Immunology, vol. 1, No. 4: 311-316.

Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." Clinical Immunology, vol. 96, No. 3: pp. 187-197.

Le Bon, A. et al. (2002). "Links between innate and adaptive immunity via type I interferon." Current Opinion Immunology, vol. 14, No. 4: pp. 432-436.

Lee, P. P. et al. (1997). "T Helper 2-Dominant Antilymphoma Immune Response Is Associated With Fatal Outcome." Blood, vol. 90, No. 4: pp. 1611-1617.

Levine, B.L. et al. (1997). "Effects of CD28 Costimulation on Long-Term Proliferation of CD4+ T Cells in the Absence of Exogenous Feeder Cells." The Journal of Immunology, vol. 159, No. 12: pp. 5921-5930.

Li, L. et al. (1998). "Cyclophosphamide Given After Active Specific Immunization Augments Antitumor Immunity by Modulation of Th1 Commitment of CD4+ T Cells." Journal of Surgical Oncology, vol. 67, No. 4: pp. 221-227.

Liebowitz, D.N. et al. (1998). "Costimulatory approaches to adoptive immunotherapy." Current Opinion Oncology, vol. 10, No. 6: pp. 533-541.

Lowes, M. A., G. A. Bishop, et al. (1997). "T helper 1 cytokine mRNA is increased in spontaneously regressing primary melanomas." J Invest Dermatol 108(6): 914-9.

Ludviksson, B. R. et al. (2000). "The effect of TGF-$\beta$1 on immune responses of naive versus memory CD4+ Th1/Th2 T cells." Eur J Immunol, vol. 30, No. 7: pp. 2101-2111.

Lum, L.G. et al (2001). "Immune modulation in cancer patients after adoptive transfer of ani-CD3/anti-CD28-costimulated T-cells—phase I clinical trial." Journal of Immunotherapy, vol. 24, No. 5: pp. 408-419.

Ma, J. et al. (1998). "Use of encapsulated single chain antibodies for induction of anti-idiotypic humoral and cellular immune responses." Journal of Pharmaceutical Sciences, Vo. 87, No. 11: pp. 1375-1378.

Maeurer, M. J., D. M. Martin, et al. (1995), "Host immune response in renal cell cancer: interleukin-4 (IL-4) and IL-10 mRNA are frequently detected in freshly collected tumor-infiltrating lymphocytes." Cancer Immunol Immunother 41(2): 111-21.

Maus, M. V. et al. (2002). "Ex vivo expansion of polyclonal and antigen-specific cytotoxic T lymphocytes by artificial APCs expressing ligands for the T-cell receptor, CD28 and 4-1BB." Nature Biotechnology, vol. 20, No. 2: pp. 143-148.

Menetrier-Caux, C. et al. (1999). "Renal cell carcinoma induces interleukin 10 and prostaglandin E2 production by monocytes." British Journal of Cancer, vol. 79, No. 1: pp. 119-130.

Moran, M. et al. (1998). "Engagement of GPI-Linked CD48 Contributes to TCR Signals and Cytoskeletal Reorganization: A Role for Lipid Rafts in T Cell Activation." Immunity, vol. 9, No. 6: 787-796.

Muller, M. et al. (2003). "Surface modification of PLGA microspheres." Journal of Biomedic Material Research, vol. 66A, No. 1: pp. 55-61.

Nabioullin, R. et al. (1994). "Interleukin-10 is a potent inhibitor of tumor cytotoxicity by human monocytes and alveolar macrophages." Journal of Leukocyte Biology, vol. 55, No. 4: pp. 437-442.

Nakagomi, H. et al. (1995). "Lack of Interleukin-2 (IL-2) Expression and Selective Expression of IL-10 mRNA in Human Renal Cell Carcinoma." Int. Journal of Cancer, vol. 63, No. 3: pp. 366-371.

Nishimura, T. et al. (2000). "The critical role of Th1-dominant immunity in tumor immunology." Cancer Chemother Pharmacol, vol. 46 (Suppl): S52-S61.

Nitta, T., M. Hishii, et al. (1994). "Selective expression of interleukin-10 gene within glioblastoma multiforme." Brain Res 649(1-2): 122-8.

O'Donnell P.B. et al. (1997). "Preparation of microspheres by the solvent evaporation technique." Advanced Drug Delivery Reviews, vol. 28, No. 1: pp. 25-42.

Oka, H. et al. (1999). "An immunomodulatory arabinomannan extracted from *Mycobacterium tuberculosis*, Z-100, restores the balance of Th1/Th2 cell responses in tumor bearing mice." Immunology Letters, vol. 70, No. 2: pp. 109-117.

Okamoto, T. et al. (1997). "Local Injection of OK432 Can Augment the TH1-Type T-Cell Response in Tumor-Draining Lymph Node Cells and Increase Their Immunotherapeutical Potential." International Journal of Cancer, vol. 70, No. 5: pp. 598-605.

Okutomi, T., Y. Kato, et al. (2000). "[Clinical effects of adjuvant therapy using Z-100 (Ancer 20 injection) for oral cancer—prevention of stomatitis and hematopoietic impairment]." Gan To Kagaku Ryoho 27(1); 65-71.

Onishi, T. et al. (1999). "An assessment of the immunological environment based on ritratumoral cytokine production in renal cell carcinoma." BJU International, vol. 83, No. 4: pp. 488-492.

Raghupathy, R. (1997). "Th1-type immunity is incompatible with successful pregnancy." Immunology Today, vol. 18, No. 10: pp. 478-482.

Raghupathy, R. et al. (1999). "Maternal Th1- and Th2-Type Reactivity to Placental Antigens in Normal Human Pregnancy and Unexplained Recurrent Spontaneous Abortions." Cellular Immunology, vol. 196, No. 2: pp. 122-130.

Rondon, G., S. Giralt, et al. (1996). "Graft-versus-leukemia effect after allogeneic bone marrow transplantation for chronic lymphocytic leukemia." Bone Marrow Transplant 18(3): 669-72.

Rosenberg, S. A. (2001). "Progress in the development of immunotherapy for the treatment of patients with cancer." Journal of Internal Medicine, vol. 250, No. 6: pp. 462-475.

Roussel, E. et al. (1996). "Predominance of a type 2 intratumoural immune response in fresh tumour-infiltrating lymphocytes from human gliomas." Clinical and Experimental Immunology, vol. 105, No. 2: pp. 344-352.

Rubbi, C.P. et al. (1993). "Evidence of surface antigen detachment during incubation of cells with immunomagnetic beads." Journal of Immunology Methods, vol. 166, No. 2: pp. 233-241.

Santin, A. D. et al. (2000). "Interleukin-10 Increases Th1 Cytokine Production and Cytotoxic Potential in Human Papillomavirus-Specific CD8(+) Cytotoxic T Lymphocytes." Journal of Virology, vol. 74, No. 10: pp. 4729-4737.

Sato, M., S. Goto, et al. (1998). "Impaired production of Th1 cytokines and increased frequency of Th2 subsets in PBMC from advanced cancer patients." Anticancer Res 18(5D): 3951-5.

Saxton, M. L. et al. (1997). "Adoptive Transfer of Anti-CD3-Activated CD4+ T Cells Plus Cyclophosphamide and Liposome-Encapsulated Interleukin-2 Cure Murine MC-38 and 3LL Tumors and Establish Tumor-Specific Immunity." Blood, vol. 89, No. 7: pp. 2529-2536.

Shibuya, T.Y. et al. (2000). "Anti-CD3/Anti-CD28 Bead Stimulation Overcomes CD3 Unresponsiveness in Patients With Head and Neck Squamous Cell Carcinoma." Arch Otolaryngol Head Neck Surg, vol. 126, No. 4: 473-479.

Shinomiya, Y., M. Harada, et al. (1995). "Anti-metastatic activity induced by the in vivo activation of purified protein derivative (PPD)-recognizing Th1 type CD4+ T cells." Immunobiology 193(5): 439-55.

Shurin, M. R., L. Lu, et al. (1999). "Th1/Th2 balance in cancer, transplantation and pregnancy." Springer Semin Immunopathol 21(3): 339-59.

Slavin, S. et al. (2001). "Non-myeloablative allogeneic Stem cell transplantation focusing on immunotherapy of life-threatening malignant and non-malignant diseases." Critical Reviews Oncology Hematology, vol. 39, No. 1-2: pp. 25-29.

Slavin, S. et al. (1995). "Allogeneic cell therapy for relapsed leukemia after bone marrow transplantation with donor peripheral blood lymphocytes." Experimental Hematology, vol. 23, No. 14: pp. 1553-1562.

Slavin, S. et al. (1996). "Allogeneic Cell Therapy With Donor Peripheral Blood Cells and Recombinant Human Interleukin-2 to Treat Leukemia Relapse After Allogeneic Bone Marrow Transplantation." Blood, vol. 87, No. 6: pp. 2195-1204.

Slavin, S. et al. (1996). "Allogeneic Cell Therapy: the Treatment of Choice for All Hematologic Malignancies Relapsing Post BMT." Blood, vol. 87, No. 9: pp. 4011-4013.

Slavin, S. et al. (2001), "Nonmyeloablative stem cell transplantation for the treatment of cancer and life-threatening nonmalignant disorders: past accomplishments and future goals." Cancer Chemother Pharmacol, vol. 48, (Suppl 1): pp. S79-S84.

Slavin, S. et al. (1998). "Immunotherapy in conjunction with autologous and allogeneic blood or marrow transplantation in lymphoma." Annals of Oncology, vol. 9 (Suppl 1): pp. S31-S39.

Smith, D. R., S. L. Kunkel, et al. (1994). "Production of interleukin-10 by human bronchogenic carcinoma." Am J Pathol 145(1): 18-25.

Smyth, M. J. et al. (2002). "New Aspects of Natural-Killer-Cell Surveillance and Therapy of Cancer." Nature Reviews Cancer, vol. 2, No. 11: pp. 850-861.

Sredni, B. et al. (1995). "Bone Marrow-Sparing and Prevention of Alopecia by AS101 in Non-Small-Cell Lung Cancer Patients Treated with Carboplatin and Etoposide." Journal of Clinical Oncology, vol. 13, No. 9: pp. 2342-2353.

Sredni, B. et al. (1996). "Predominance of TH1 Response in Tumor-Bearing Mice and Cancer Patients Treated with AS101." National Journal of Cancer Institute, vol. 88, No. 18: pp. 1276-1284.

Sredni, B., R. H. Xu, et al. (1996). "The protective role of the immunomodulator AS101 against chemotherapy-induced alopecia studies on human and animal models." Int J Cancer 65(1): 97-103.

Stein, G., W. Henn, et al. (1998). "Modulation of the cellular and humoral immune responses of tumor patients by mistletoe therapy." Eur J Med Res 3(4): 194-202.

Stern, B. V. et al. (2002). "Vaccination with Tumor Peptide in CpG Adjuvant Protects Via IFN-Gamma-Dependent CD4 Cell Immunity." The Journal of Immunology, vol. 168, No. 12: pp. 6099-6105.

Tabata, T. et al. (1999). "Th2 Subset Dominance Among Peripheral Blood T Lymphocytes in Patients with Digestive Cancers." American Journal of Surgery, vol. 177, No. 3: pp. 203-208.

Taga, K. et al. (1993). "Human Interleukin-10 Can Directly Inhibit T-Cell Growth." Blood, vol. 81, No. 11: pp. 2964-2971.

Takeuchi, T. et al. (1997). "Th2-like response and antitumor effect of anti-interleukin-4 mAb in mice bearing renal cell carcinoma." Cancer Immunol Immunother, vol. 43, No. 6: pp. 375-381.

Tanaka, K. K. Kemmotsu, et al. (1998). "[Flow cytometric analysis of helper T cell subsets (Th1 and Th2) in healthy adults]." Rinsho Byori 46(12): 1247-51.

Tanaka, J., M. Imamura, et al. (1997). "The important balance between cytokines derived from type 1 and type 2 helper T cells in the control of graft-versus-host disease." Bone Marrow Transplant 19(6): 571-6.

Tatsumi, T. et al. (2002). "Disease-associated bias in T helper type 1 (Th1)/Th2 CD4(+) T cell responses against MAGE-6 in HLA-DRB10401(+) patients with renal cell carcinoma or melanoma." Journal of Experimental Medicine, vol. 196, No. 5: pp. 619-628.

Terao, H., M. Harada, et al. (1994). "Th1 type CD4+ T cells may be a potent effector against poorly immunogenic syngeneic tumors." Biotherapy 8(2): 143-51.

Tessmar, J. et al. (2003). "The use of poly(ethylene glycol)-block-poly(lactic acid) derived copolymers for the rapid creation of biomimetic surfaces." Biomaterials, vol. 24, No. 24: pp. 4475-4486.

Thanhauser, A., A. Bohle, et al. (1995). "The induction of bacillus-Calmette-Guerin-activated killer cells requires the presence of monocytes and T-helper type-1 cells." Cancer Immunol Immunother 40(2): 103-8.

Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." Clinical Immunology, vol. 105, No. 3: pp. 259-272.

Thomas, E., R. Storb, et al. (1975). "Bone-marrow transplantation (first of two parts)." N Engl J Med 292(16): 832-43.

Thomas, E. D., R. Storb, et al. (1975). "Bone-marrow transplantation (second of two parts)." N Engl J Med 292(17): 895-902.

Tilg, H. et al. (1994). "Interleukin-6 (IL-6) as an Anti-inflammatory Cytokine: Induction of Circulating IL-1 Receptor Antagonist and Soluble Tumor Necrosis Factor Receptor p55." Blood, vol. 83, No. 1: pp. 113-118.

To, W. C. et al. (2000). "Therapeutic Efficacy of Th1 and Th2 L-selectin—CD4+ Tumor-Reactive T Cells." Laryngoscope vol. 110, (10 Pt 1): pp. 1648-1654.

Ueno, N. T., G. Rondon, et al. (1998). "Allogeneic peripheral-blood progenitor-cell transplantation for poor-risk patients with metastatic breast cancer." J Clin Oncol 16(3): 986-93.

van Besien, K., P. Thall, et al. (1997). "Allogeneic transplantation for recurrent or refractory non-Hodgkin's lymphoma with poor prognostic features after conditioning with thiotepa, busulfan, and cyclophosphamide: experience in 44 consecutive patients." Biol Blood Marrow Transplant 3(3): 150-6.

Voutsadakis, I. A. (2003). "NK cells in allogeneic bone marrow transplantation." Cancer Immunol Immunother, vol. 52, No. 9: pp. 525-534.

Vowels, B. R. et al. (1994). "Th2 Cytokine mRNA Expression in Skin in Cutaneous T-Cell Lymphoma." The Journal of Investigative Dermatology, vol. 103, No. 5: pp. 669-673.

Wang, Q. et al. (1995). "Selective Cytokine Gene Expression in Renal Cell Carcinoma Tumor Cells and Tumor-Infiltrating Lymphocytes." International Journal of Cancer, vol. 61, No. 6: pp. 780-785.

Weber, K., U. Mengs, et al. (1998). "Effects of a standardized mistletoe preparation on metastatic B16 melanoma colonization in murine lungs." Arzneimittelforschung 48(5): 497-502.

Weiden, P. L. et al. (1981). "Antileukemic Effect of Chronic Graft-Versus-Host Disease: Contribution to Improved Survival After Allogeneic Marrow Transplantation." New England Journal of Medicine, vol. 304 No. 25: pp. 1529-1533.

Whitmore, M. et al. (1999). "LPD lipopolyplex initiates a potent cytokine response and inhibits tumor growth." Gene Therapy, vol. 6, No. 11: pp. 1867-1875.

Wong, B. R. et al. (1999). "TRANCE is a TNF family member that regulates dendritic cell and osteoclast function." Journal of Leukocyte Biology, vol. 65, No. 6: pp. 715-724.

Woo, E. Y. et al. (2001). "Regulatory CD4(+)CD25(+) T Cells in Tumors from Patients with Early-Stage Non-Small Cell Lung Cancer and Late-Stage Ovarian Cancer." Cancer Research, vol. 61, No. 12: pp. 4766-4772.

Woo, E. Y. et al. (2002). "Cutting edge: Regulatory T Cells from Lung Cancer Patients Directly Inhibit Autologous T cell proliferation." J Immunol 168(9): 4272-6.

Yamamura, M. (1992). "Defining protective responses to pathogens: cytokine profiles in leprosy lesions." Science 255 (5040): 12.

Yashiro-Ohtani, Y. et al. (2000). "Non-CD28 Costimulatory Molecules Present in T Cell Rafts Induce T Cell Costimulation by Enhancing the Association of TCR with Rafts." The Journal of Immunology, vol. 164, No. 3: pp. 1251-1259.

Yoon, T. J. et al. (1998). "Prophylactic effect of Korean mistletoe (Viscum album coloratum) extract on tumor metastasis is mediated by enhancement of NK cell activity." International Journal of Immunopharmacology, Vo. 20, No. 4-5: pp. 163-172.

Zitvogel, L. et al. (1996). "Therapy of Murine Tumors with Tumor Peptide-Pulsed Dendritic Cells: Dependence on T Cells, 87 Costimulation, and T Helper Cell 1-associated Cytokines." Journal of Experimentive Medicine, vol. 183, No. 1: pp. 87-97.

Meier et al: "Development of a Latex Conjugated immuno Cytological Marker for Scanning Electron Microscopic Analysis of Quail Chick Chimeras", Journal of Experimental Zoology, vol. 224, No. 1, 1982, pp. 25-38.

Dinauer et al: "Selective Targeting of Antibody-Conjugated Nanoparticles to Leukemic Cells and Primary T-Lymphocytes", Biomaterials, vol. 26, No. 29, Oct. 2005, pp. 5898-5906.

Sinha et al.: "Biodegradable Microspheres for Protein Delivery", Journal of Controlled Release, vol. 90, No. 3, Jul. 31, 2003, pp. 261-280.

Supplementary European Search Report, Jan. 20, 2010.

Encke et al., "Prophylactic and therapeutic vaccination with dendritic cells against hepatitis C virus infection", Clinical and Experimental Immunology, 2005, vol. 142, pp. 362-269.

Gong et al., "Fusions of human ovarian carcinoma cells with autologous or allogeneic dendritic cells induce antitumor immunity", The Journal of Immunology, 2000, vol. 165, pp. 1705-1711.

Har-Noy, "Completely mismatched allogeneic CD3/CD28 cross-linked Th1 memor cells elicit anti-leukemia effects in unconditioned hosts without GVHD toxicity", 2008, Leukemia Research, vol. 32, No. 12, pp. 1903-1913.

* cited by examiner

DEVICE FOR ENHANCING IMMUNOSTIMULATORY CAPABILITIES OF T-CELLS

The present application is a divisional of and claims priority of U.S. patent application Ser. No. 11/066,133, filed Feb. 24, 2005, the content of which is hereby incorporated by reference in its entirety.

The present application is based on and claims the benefit of U.S. provisional patent application Ser. No. 60/547,966, filed Feb. 26, 2004, the content of which is hereby incorporated by reference in its entirety.

FIELD OF INVENTION

This invention relates to methods for generating T-cells with enhanced immunostimulatory capabilities for use in cell therapy treatment protocols.

BACKGROUND OF THE INVENTION

Cell therapy methods have been developed in order to enhance the host immune response to tumors, viruses and bacterial pathogens. Cell therapy methods often involve the ex-vivo activation and expansion of T-cells. Examples of these type of treatments include the use tumor infiltrating lymphocyte (TIL) cells (see U.S. Pat. No. 5,126,132 issued to Rosenberg), cytotoxic T-cells (see U.S. Pat. No. 6,255,073 issued to Cai, et al.; and U.S. Pat. No. 5,846,827 issued to Celis, et al.), expanded tumor draining lymph node cells (see U.S. Pat. No. 6,251,385 issued to Terman), and various other lymphocyte preparations (see U.S. Pat. No. 6,194,207 issued to Bell, et al.; U.S. Pat. No. 5,443,983 issued to Ochoa, et al.; U.S. Pat. No. 6,040,177 issued to Riddell, et al.; U.S. Pat. No. 5,766,920 issued to Babbitt, et al.).

For maximum effectiveness of T-cells in cell therapy protocols, the ex vivo activated T-cell population should be in a state that can maximally orchestrate an immune response to cancer, infectious diseases, or other disease states. For an effective T-cell response, the T-cells first must be activated. For activation, at least two signals are required to be delivered to the T-cells. The first signal is normally delivered through the T-cell receptor (TCR) on the T-cell surface. The TCR first signal is normally triggered upon interaction of the TCR with peptide antigens expressed in conjunction with an MHC complex on the surface of an antigen-presenting cell (APC). The second signal is normally delivered through co-stimulatory receptors on the surface of T-cells. Co-stimulatory receptors are generally triggered by corresponding ligands or cytokines expressed on the surface of APCs.

Due to the difficulty in maintaining large numbers of natural APC in cultures of T-cells being prepared for use in cell therapy protocols, alternative methods have been sought for ex-vivo activation of T-cells. One method is to by-pass the need for the peptide-MHC complex on natural APCs by instead stimulating the TCR (first signal) with polyclonal activators, such as immobilized or cross-linked anti-CD3 or anti-CD2 monoclonal antibodies (mAbs) or superantigens. The most investigated co-stimulatory agent (second signal) used in conjunction with anti-CD3 or anti-CD2 mAbs has been the use of immobilized or soluble anti-CD28 mAbs.

The combination of anti-CD3 mAb (first signal) and anti-CD28 mAb (second signal) immobilized on a solid support such as paramagnetic beads (see U.S. Pat. No. 6,352,694 issued to June, et al.) has been used to substitute for natural APCs in inducing ex-vivo T-cell activation in cell therapy protocols (Levine, Bernstein et al. 1997; Garlie, LeFever et al. 1999; Shibuya, Wei et al. 2000). While these methods are capable of achieving therapeutically useful T cell populations, the use of paramagnetic beads makes the ease of preparation of T-cells less than ideal. Problems include the high cost of the beads, the labor-intensive process for removing the beads prior to cell infusion, and the inability of the beads to activate CD8 T-cell subsets (Deeths, Kedl et al. 1999; Laux, Khoshnan et al. 2000). In addition, the T-cell populations resulting from this method, and other prior art T-cell stimulation methods, lack the type of robustness required for eliciting effective immune stimulation when infused into patients. As a consequence, no prior art cell therapy protocols have demonstrated significant efficacy in clinical settings.

This has motivated the search for more effective methods for activating T-cells for use in cell therapy protocols. One such method is the use of APC tumor cell lines that have been genetically modified to express receptors that bind mAbs. These modified APC can be loaded with anti-CD3 and anti-CD28 mAbs (Thomas, Maus et al. 2002) or additionally modified to express the ligand for 4-1BB (Maus, Thomas et al. 2002) and then used to activate T-cells for use in cell therapy protocols. It was found that these modified APCs resulted in more effective activation of T-cell populations than the use of CD3/CD28-coated paramagnetic beads. However, the use of genetically-manipulated tumor cell lines in cell therapy protocols raises safety concerns which limit the commercial application of this technique.

SUMMARY OF THE INVENTION

In this situation, biodegradable supports coated with a first material that is capable of cross-linking second materials with reactivity to moieties on the surface of T-cells are utilized. The coated biodegradable supports are then mixed with second material labeled T-cells. The signals delivered by the cross-linked second materials are enhanced by centrifugation of the mixture. The signals are further enhanced by the culture of the mixture at high cell densities.

The present invention also includes biodegradable devices that have a biodegradable support with one or more agents that are reactive to T-cell moieties. Such agents deliver signals to T-cells to enhance immunostimulatory or immunoregulatory capabilities.

DETAILED DESCRIPTION OF THE PREFERRED EMBODIMENTS

There is a need for improved T-cell stimulation methods capable of increasing the robustness of T-cells for use in cell therapy protocols that are more suitable for use in human therapy.

In order to improve the robustness of T-cells, it is also desirable that the improved stimulation methods as closely as possible mimic the stimulatory effects of natural APCs. The improvement in T-cell activation observed with the CD3/CD28-coated APC cell lines discussed above (Thomas, Maus et al. 2002); (Maus, Thomas et al. 2002), was attributed to the availability of ligands to co-stimulatory molecules naturally expressed on the APC cell line that worked in concert with the CD3/CD28 stimulation. These ligands included B7-H3, PD-L1, PD-L2 and IL-15.

Therefore, it is desired to have a method for improved T-cell stimulation capable of presenting a multiplicity of co-stimulatory ligands without the requirement for use of a tumor cell line.

Natural APCs, however, not only provide multiple simultaneous stimuli to T-cells, they provide different arrays of multiple stimuli at different times and/or stages in the T-cell response to T-cell stimulation. No prior art T-cell stimulation methods are capable of mimicking this natural process.

The ability to mimic this natural process would provide a means to control not only the expansion of T-cells, but also the differentiation of T-cells. In the process of T-cell differentiation into regulatory or effector cells, different signals are required at different times and/or stages in the T-cell response to APC stimulation. Thus, it would be desirable to be able to create ex-vivo conditions that mimic this natural process in order to provide a greater variety of differentiated cells for use in cell therapy, including cells which could either stimulate immunity or suppress immunity.

The maintenance of the high density cell cultures used in the present invention require special care, as the degradation of the biological supports causes a fall in the media pH and the higher cell densities result in rapid accumulation of metabolic waste products and consumption of nutrients in the culture medium. For these reasons, media changes are required at least daily and preferably at least twice daily after the cells obtain a cell density in excess of 1 million per ml.

Frequent media changes can remove endogenous cytokines that are important for the maintenance and growth of the T-cell cultures. Therefore, in preferred embodiments, the removed culture media is filtered through a dialysis membrane in order to remove metabolic waste products, but retain endogenous cytokines. The retained media is then supplemented with fresh nutrient media and returned to the mixed culture. This enables the cells to be exposed to fresh nutrient media without dilution of the endogenous cytokines.

As the T-cells grow and mature in the cultures, various arrays of second materials can be added to the cultures at any time as required and subsequently cross-linked by mixing with additional coated biodegradable supports. Alternatively, the second materials can be added to the biodegradable supports and the coated supports added at various times to the cultures. Centrifugation of the mixture each time after adding additional second materials and coated biodegradable supports provides added benefit. In preferred embodiments, the centrifugation step is conducted daily to coincide with the media dialysis step.

Biodegradable Spheres

Aliphatic polyesters, such as polylactic acid) (PLA), poly (glycolic acid) (PGA), copolymers of PLA and PGA (PLGA) or poly(carprolactone) (PCL), and polyanhydrides are preferred materials for use as biodegradable polymers for the supports. The polymers can be formulated as various shapes, such as films, strips, fibers, gels, nanospheres or microspheres, and then coated with a first material. Microspheres are a preferred formulation because they can be reproducibly manufactured into small microsphere particle sizes of 1.to.500 microns, preferably 1 to 10 microns and most preferably 1 to 5 microns. Microspheres of this size range are capable of direct injection into the body by conventional methods. It is preferred that the coated microspheres be formulated to degrade in culture media or physiological fluids within 14 days, more preferably within 7 days, and most preferably within 3 days. In other preferred methods, nanospheres are formulated. These devices are preferred in applications where very rapid degradation, for example 3 days or less is required.

One preferred first material for coating on the biodegradable microspheres is polyclonal goat (or sheep) anti-mouse polyclonal antibodies. By way of example, this preferred first material can be used to cross-link mouse-derived monoclonal antibodies, or fragments or genetically engineered derivatives thereof, that have specificity for T-cell surface moieties. Thus, for example, the mixing of goat anti-mouse coated microspheres (or nanospheres) with human T-cells labeled with mouse anti-human CD3 and mouse anti-human CD28 mAbs will cause the cross-linking of the mouse mAbs on the human T-cells through the binding of the goat anti-mouse polyclonal antibody with the mouse mAbs. The cross-linking of the mAbs causes the activation and proliferation of the T-cells. Many combinations of first materials and second materials can be used to accomplish the objective of cross-linking second agents attached to T-cell surface moieties in order to initiate signal transduction and activation of T-cells. Alternatively, the second materials can be added to the biodegradable supports prior to addition to the T-cells.

The coated biodegradable microspheres (or nanospheres) used in the present invention provide many advantages for preparation of T-cells for use in cell therapy protocols over prior art methods where mitogenic agents are immobilized on a solid surface, such as paramagnetic beads:

First, since the devices are biocompatible and naturally degrade into non-toxic substances, there is no need to institute a bead removal process.

Second, because the devices have a low density, they can be used with cells being subjected to a centrifugal force. Prior art devices, such as paramagnetic beads, cause damage to cells when subjected to centrifugation. The ability to centrifuge cells with the beads permits the use of centrifugal force to enhance the quality of signals provided to the T-cells by stimulatory ligands cross-linked on the surface of the T-cells and also provides a means to wash and otherwise process the T-cells for preparation for infusion.

Third, in one use of the present invention, rather than immobilizing T-cell stimulatory and co-stimulatory ligands to a solid surface to present signals to T-cells, the use of a coated biodegradable microspheres (or nanospheres) permits the ligands to be first applied to the T-cells and then the labeled T-cells to be mixed with the coated biodegradable microspheres (or nanospheres). In this manner, the coated microspheres (or nanospheres) act as a universal cross-linking agent.

Fourth, as a universal cross-linking agent, a multiplicity of stimulatory and co-stimulatory ligands can be applied to T-cells and be cross-linked by the coated beads and the composition of the multiplicity of stimulatory and co-stimulatory ligands to be cross-linked can be varied over time.

Fifth, the ability to vary the composition of the array of stimulatory and co-stimulatory signals provided to T-cells over time permits the practice of methods designed to mimic natural presentation of T-cell proliferation, differentiation and functional signals.

Sixth, the ability to mimic the natural signal presentation to T-cells permits the development of T-cells with a multitude of functional characteristics for use in cell therapy protocols.

Seventh, the ability to control the sequence and variety of signals delivered to T-cells over time permits a means to control the differentiation pathways of T-cells ex-vivo. This will permit experimentation with novel combinations and sequencing of signals delivered to T-cells. Such methods will lead to T-cell products with novel effector functions both stimulatory and suppressive for use in cell therapy protocols.

For the purposes of the present invention, all references to T-cells includes a population of cells with at least a portion of the cells containing T-cells. T-cells are cells which express TCR, including α/β and γ/δ TCRs. T-cells include all cells which express CD3, including T-cell subsets which also express CD4 and CD8. T-cells include both naïve and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage.

Increased Signal Transduction

One aspect of the present invention provides methods for enhanced stimulation of a population of T-cells by the concentration of a mixture of first material coated biodegradable microspheres (or nanospheres) and second material labeled T-cells. In order to increase the efficacy of the signal transduced to the T-cells, it is important to both increase the quantity of second agents cross-linked and the quality of the cross-linking.

In order to assure the highest quantity of second materials that are associated with the corresponding surface moieties on the surface of the T-cells, the labeling of the T-cells should be conducted with excess second materials. In a preferred embodiment where mouse mAbs to human T-cell surface antigens are the second materials, the mAbs are preferably mixed with a T-cell suspension whereby the T-cells are at a concentration of $1\times10^6$ to $1\times10^7$ per ml and each mAb is at a concentration of 0.5 µl/ml to 10 µl/ml, preferably 1 µl/ml. The labeled T-cells should be mixed with the coated biodegradable spheres at a ratio of at least one sphere per cell, and preferably at a ratio of 3 spheres per cell.

In order to assure the highest quality of cross-linking, the labeled cells and the coated biodegradable spheres are preferably first mixed thoroughly and then concentrated together under centrifugal force. The centrifugation is preferably conducted every 3 days, more preferably at least once daily. It is also preferable that the T-cells be kept at 4° C. from the time new mAbs are added through the completion of the centrifugation. Keeping the cells at refrigeration temperature prevents the capping and shedding of the ligated T-cell surface receptors prior to being cross-linked.

Cell Culture Methods

It is preferable to maintain processive and sustained TCR signal transduction and co-simulation in order to provide the most robust T-cells for use in cell therapy protocols. For this reason, the methods of the present invention work best when the cultured T-cells are maintained at high cell densities, such as greater than $10^6$ cells/ml, or more preferably greater than $10^7$ cells/ml, or most preferably greater than $10^8$ cells/ml. The high cell densities increase the cell:cell interaction and the interaction with the biodegradable spheres.

The increased cell:cell interaction has a beneficial effect that is separate from the cross-linking effect of the biodegradable spheres. The beneficial effect comes from the expression of stimulatory ligands which upregulate on the surface of T-cells in response to maximal activation conditions. These ligands interact with the corresponding receptors on other T-cells. For example, T-cells will express one or more of the following TNFR co-stimulatory ligands such as LIGHT, CD70, OX40L, 4-1BBL and CD30L after maximal activation.

Maintaining cells at high densities in culture with biodegradable spheres requires the frequent changing of the culture media. The high cell densities result in a high rate of build up of metabolic waste products and consumption of available nutrients. In addition, the hydrolysis of the biodegradable spheres causes the pH of the culture media to become acidic. Too rapid media replacement, however, can be detrimental to cultures where exogenous cytokines are not utilized. It is preferable not to use exogenous cytokines when processing cells for use in cell therapy protocols, as exogenous cytokines can be toxic when infused into humans and can make the cultured cells dependant upon the presence of the exogenous cytokines for viability. Therefore, the methods of the present invention include a dialysis step in the cell processing.

Dialysis of the culture medium with membrane pore size of 10,000 dalton or less will enable retention of endogenous cytokines while allowing passage of metabolic waste. In preferred embodiments, half the culture medium of a culture is removed daily and 90% passed through a dialysis filter. The media passed through the filter is discarded, while the retained media is brought up to the original volume with fresh culture media.

According to the method of the present invention, a process is described for producing T-cells with robustness and enhanced function for use in cell therapy protocols involving: (1) the labeling of a population of T-cells with one or more agents that have reactivity to cell surface moieties; (2) mixing of the population of labeled T-cells with coated biodegradable spheres capable of cross-linking the agents attached to cell surface moieties on the T-cells causing a signal to be transduced to the T-cells; (3) concentrating of the mixture by centrifugation; (4) continued culture of the T-cells at high cell density; and (5) removal of media from the cultures at least daily and the dialysis of the media for retention of endogenous cytokines and replacement with fresh media; and (6) repeat of the process as necessary with the same or different agents for labeling of the T-cells in order to generate both the quantities of T-cells necessary for infusion and the optimal function of the T-cells for clinical effect.

Choice of T-Cell Ligating Targets

The ability to design more efficient and effective T-cell activation, expansion and differentiation methods will be a direct result of the selection and timing of application of second materials. Second materials are agents which are capable of ligating T-cell surface moieties and delivering a signal to the T-cell upon cross-linking. These materials are preferably monoclonal antibodies, or fractions or genetically manipulated versions thereof, such as fusion proteins. The selection of second materials will be as a result of understanding of the T-cell activation, expansion and differentiation process and the requirements for the type and duration of signals at any one time in the life of the responding T-cells.

It is known that at least two type of receptors need to be engaged for T-cell activation, the TCR and a co-stimulator (Chambers and Allison 1999). In response to natural APC engagement with antigenic peptide and co-stimulatory ligands, the contact site of the APC and T-cell forms an "immunological synapse". The synapse assembles into topologically and spatially distinct regions. The initial TCR engagement occurs at the periphery of the synapse (Grakoui, Bromley et al. 1999) after which ligand engagement of co-simulating molecules such as CD28, CD2, CD48 and LFA-1 facilitates the sorting and re-arrangements of receptors at the synapse. The content of molecules at the synapse can be specifically enriched in a subset of proteins and can selectively exclude proteins. This selective movement of proteins is facilitated by structures known as "lipid rafts".

Lipid raft membrane partitioning is known to be crucial for optimal TCR signal transduction (Moran and Miceli 1998; Janes, Ley et al. 1999) and co-stimulators to TCR signaling cause the synapse formation and the re-organization and clustering of lipid rafts at the synapse. These events provide a natural mechanism for integrating spatial and temporal information provided to T-cells from the environment.

Accordingly, knowledge of the types of receptors available at the synapse in response to defined stimuli can provide the information for deciding the various types of co-stimulators to utilize over a period of time. Lipid rafts function as platforms for the concentration and juxtaposition of TCR associated signal transducers and assembly of an organized TCR signaling complex. Thus, by a process of first providing a defined array of signals to a population of T-cells and next analyzing the proteins assembled in lipid rafts that were induced by the first array, a second array of possible signals can be determined. The process can be repeated with second array stimulators. After application of the second array, the process can be repeated with a third array and so on. At each step in the process, the response of the T-cells can be monitored in order to optimize for the desired function, such as proliferation, the types and quantities of selected cytokine production, the expression of effector molecules and other functional surface molecules.

For example, both CD2 and LFA-1 are raft associated proteins that can stimulate initial T-cell activation in the absence of CD28 engagement (Yashiro-Ohtani, Zhou et al. 2000). The engagement of these molecules is known to upregulate and increase avidity for receptors for ICAM-1 which could then be engaged in a second array. CD2/LFA-1 engagement are know to facilitate T-cell activation by increasing the number of TCRs engaged over time, whereas CD28 functions by increasing the potency of those TCRs that are engaged, thus lowering the number of TCRs that need to be engaged in order to effect a response (Bachmann, McKall-Faienza et al. 1997).

In preferred embodiments, a first array including CD3 and other co-stimulatory molecules selected from one or more of the following: CD2, CD28, CD48, LFA-1, CD43, CD45, CD4, CD8, CD7, GM1, LIGHT (HVEM fusion protein) is utilized. A second array including CD3 and one or more of the first array co-stimulators with the additional choices of the following inducible co-stimulatory ligands: CD27, OX40, 4-1BB and CD30.

Also in preferred embodiments, T-cell counter receptors to various adhesion molecules can be engaged during the process. Examples of adhesion molecules on T-cells are: CD44, CD31, CD18/CD11a (LFA-1), CD29, CD54 (ICAM-1), CD62L (L-selectin), and CD29/CD49d (VLA-4). Other suitable second array agents include non-cytokine agents which bind to cytokine receptors and deliver a signal when cross-linked. Examples of these type of agents are mAbs to cytokine receptors including: IL-2R, IL-4R, IL-10R, Type II IFNR1 and R2, Type I IFNR, IL-12Rbeta1 and beta2, IL-15R, TNFR1 and TNFR2, and IL-1R. Also any agents capable of binding to chemokine receptors on T-cells and delivering a signal when cross-linked, including those in the C—C and C—X—C categories. Examples of chemokine receptors associated with T-cell function include CCR1, CCR2, CCR3, CCR4, CCR5, and CXCR3

EXAMPLE METHODS

Examples of optimized processes for producing a T-cell population with enhanced ability to stimulate the immune system follow. All examples utilize goat anti-mouse coated biodegradable microspheres and T-cells labeled with mouse mAbs specific for T-cell surface antigens:

Example #1

Set-up (Day 0)
(1) collection of leukocytes by leukapheresis;
(2) purification of $10^8$ CD4+ T-cells by positive selection;
(3) labeling of purified CD4+ cells with anti-CD3, anti-CD28 and anti-IL-12Rbeta2 mAbs;
(4) mixing the labeled cells with coated microspheres in gas permeable bags (3:1 sphere:cell);
(5) suspension of the mixture at a cell density of 1×106/ml in 100 ml;
(6) centrifugation of the mixture at 500×g for 8 min at 4° C.;
(7) gently resuspend and culture in humidified atmosphere at 37° C. with 5% $CO_2$;

Day 3
(8) remove 80 ml of culture media by syringe aspiration using a 0.45 micron filter so as not to remove any cells;
(9) pass 70 ml of the removed media through a dialysis filter of 6,000 dalton cut-off size;
(10) add 70 ml of fresh culture media to the retained 10 ml and add back to the culture bag;
(11) add 100 μg each of anti-CD3, anti-CD28, anti-IL-12Rbeta2 and anti-4-1BB mAbs to the culture bag;
(12) mix coated microspheres at a sphere:cell ratio of 1:1;
(13) centrifuge mixture at 500×g for 8 min at 4° C.;
(14) gently resuspend and culture in humidified atmosphere at 37° C. with 5% $CO_2$;

Day 4
(15) repeat steps 8-10

Day 5
(16) repeat steps 8-10

Day 6
(17) repeat steps 8-14
(18) after 12 h repeat steps 8-10

Day 7
(19) repeat steps 8-10
(20) after 12 h repeat steps 8-10

Day 8
(21) repeat steps 8-10
(22) after 12 h repeat steps 8-10

Day 9
(23) harvest T-cell population and formulate for infusion

Results

This method results in a population of T-cells with enhanced proliferation and production of IFN-gamma and TNF-alpha compared to cells activated with CD3/CD28-coated immunomagnetic beads alone. N=6

| Method | Fold Expansion | IFN-gamma ng/ml | TNF-alpha ng/ml | IL-4 pg/ml |
| --- | --- | --- | --- | --- |
| Example #1 | 830 +/− 77 | 970 +/− 160 | 180 +/− 38 | <20 |
| 3/28-beads + IL-2 | 80 +/− 20 | 3 +/− 2.2 | 0.5 +/− .2 | 80 +/− 16 |

Example #2

Set-up (Day 0)
(4) collection of leukocytes by leukapheresis;
(5) purification of $10^8$ CD4+ T-cells by positive selection;
(6) labeling of purified CD4+ cells with anti-CD3, anti-CD28 mAbs;
(4) mixing the labeled cells with coated microspheres in gas permeable bags (3:1 sphere:cell);
(5) suspension of the mixture at a cell density of 1×106/ml in 100 ml;
(6) centrifugation of the mixture at 500×g for 8 min at 4° C.;
(7) gently resuspend and culture in humidified atmosphere at 37° C. with 5% $CO_2$;

Day 3
(8) remove 80 ml of culture media by syringe aspiration using a 0.45 micron filter so as not to remove any cells;
(9) pass 70 ml of the removed media through a dialysis filter of 6,000 dalton cut-off size;

(15) add 70 ml of fresh culture media to the retained 10 ml and add back to the culture bag;
(16) add 100 μg each of anti-CD3, anti-CD28, mAbs to the culture bag;
(17) mix coated microspheres at a sphere:cell ratio of 1:1;
(18) centrifuge mixture at 500×g for 8 min at 4° C.;
(19) gently resuspend and culture in humidified atmosphere at 37° C. with 5% $CO_2$;

Day 4
(15) repeat steps 8-10
Day 5
(16) repeat steps 8-10
Day 6
(24) repeat steps 8-14
(25) after 12 h repeat steps 8-10
Day 7
(26) repeat steps 8-10
(27) after 12 h repeat steps 8-10
Day 8
(28) repeat steps 8-10
(29) after 12 h repeat steps 8-10
Day 9
(30) harvest T-cell population and formulate for infusion Results This method results in a population of T-cells with enhanced proliferation and production of IFN-gamma and TNF-alpha compared to cells activated with CD3/CD28-coated immunomagnetic beads alone, as well as enhanced expression of CD40L. N=6

| Method | Fold Expansion | IFN-gamma ng/ml | TNF-alpha ng/ml | CD40L % |
|---|---|---|---|---|
| Example #2 | 630 +/− 77 | 90 +/− 16.7 | 8.8 +/− 1.3 | 78.5 +/− 10 |
| 3/28-beads + IL-2 | 80 +/− 20 | 3 +/− 2.2 | 0.5 +/− .2 | 15 +/− 6 |

Example #3

Set-up (Day 0)
(7) collection of leukocytes by leukapheresis;
(8) purification of $10^8$ CD4+ T-cells by positive selection;
(9) labeling of purified CD4+ cells with anti-CD3, anti-CD28 and anti-HVEM mAbs;
(4) mixing the labeled cells with coated microspheres in gas permeable bags (3:1 sphere:cell);
(5) suspension of the mixture at a cell density of 1×106/ml in 100 ml;
(6) centrifugation of the mixture at 500×g for 8 min at 4° C.;
(7) gently resuspend and culture in humidified atmosphere at 37° C. with 5% $CO_2$;

Day 3
(8) remove 80 ml of culture media by syringe aspiration using a 0.45 micron filter so as not to remove any cells;
(9) pass 70 ml of the removed media through a dialysis filter of 6,000 dalton cut-off size;
(20) add 70 ml of fresh culture media to the retained 10 ml and add back to the culture bag;
(21) add 100 μg each of anti-CD3, anti-CD28, anti-CD27 and anti-4-1BB mAbs to the culture bag;
(22) mix coated microspheres at a sphere:cell ratio of 1:1;
(23) centrifuge mixture at 500×g for 8 min at 4° C.;
(24) gently resuspend and culture in humidified atmosphere at 37° C. with 5% $CO_2$;

Day 4
(15) repeat steps 8-10
Day 5
(16) repeat steps 8-10
Day 6
(31) repeat steps 8-14
(32) after 12 h repeat steps 8-10
Day 7
(33) repeat steps 8-10
(34) after 12 h repeat steps 8-10
Day 8
(35) repeat steps 8-10
(36) after 12 h repeat steps 8-10
Day 9
(37) repeat steps 8-10;
(38) after 12 h repeat steps 8-10;
(39) add 100 μg each of anti-CD3, anti-CD28, and HVEM-Fc to the culture bag;
(40) mix coated microspheres at a sphere:cell ratio of 1:1;
(41) centrifuge mixture at 500×g for 8 min at 4° C.;
(42) gently resuspend and culture in humidified atmosphere at 37° C. with 5% $CO_2$;
Day 10
(43) repeat steps 8-10;
(44) after 12 h repeat steps 8-10;
Day 11
(45) harvest T-cell population and formulate for infusion.

Results

This method results in a population of T-cells with enhanced proliferation and production of IFN-gamma LIGHT and FasL compared to cells activated with CD3/CD28-coated immunomagnetic beads alone. N=6

| Method | Fold Expansion | IFN-gamma ng/ml | LIGHT (%) | FasL % |
|---|---|---|---|---|
| Example #3 | 290 +/− 21 | 44 +/− 6.2 | 38.4 +/− 3.3 | 61.4 +/− 10 |
| 3/28-beads + IL-2 | 80 +/− 20 | 3 +/− 2.2 | 6.1 +/− 5 | 4 +/− 1.3 |

Although the present invention has been described with reference to preferred embodiments, workers skilled in the art will recognize that changes may be made in form and detail without departing from the spirit and scope of the invention.

What is claimed is:

1. A device for enhancing immunostimulatory capabilities of T-cells comprising:
an universal crosslinking agent comprising a support coated with a first material, wherein the first material is capable of crosslinking more than one array of second materials, the second materials capable of binding moieties on the surface of T-cells to deliver a signal to the T-cells and wherein each successive array of second materials is added at a later time in the T-cell response than the previous array of second materials.

2. The device of claim 1 wherein each of the one or more arrays comprises one or more second materials.

3. The device of claim 1 wherein each of the one or more arrays comprises two or more second materials.

4. The device of claim 1 wherein the universal crosslinking agent is capable of crosslinking second materials bound to the T-cell surface moieties.

5. The device of claim 1 wherein an array of second materials comprises one or more antibodies that have specificity to a T-cell surface moiety.

6. The device of claim 1 wherein the first material is an antibody.

7. The device of claim 1 wherein the support is a biodegradable support.

8. The device of claim 1 wherein the support is a biodegradable microsphere.

9. The device of claim 1 wherein the support is biodegradable into a substance that is nontoxic to humans.

10. The device of claim 1 wherein the support is a microsphere that degrades in 14 days or less.

11. The device of claim 1 wherein the second materials in an array are selected from anti-CD3, -CD28, -B7-H3, -PD-L1, -PD-L2, -IL-15R, -CD2, -CD48, -LFA-1, -CD43, -CD45, -CD4, -CD8, -CD7, -GM1, -LIGHT, -CD27, -OX40, -4-1BB, -CD30, -CD44, -CD31, -CD18/CD11a, -CD29, -CD54, -CD62L, -VLA4, -IL-2R, -IL-4R, IL-10R, -type II IFNR1 and R2, -type I IFNR, -IL-12beta1 and beta2, -IL-15R, -TNFR1, -TNFR2, and -IL-1R.

12. The device of claim 1 wherein the first material crosslinks at least two arrays of second materials, each array comprising at least two second materials and wherein the second array is added at a later time in the T-cell response than the first array.

13. The device of claim 1 wherein the first material crosslinks more than two arrays of second materials, each array comprising at least two second materials and wherein each successive array is added at a later time in the T-cell response than the previous array.

* * * * *